United States Patent [19]

Badran

[11] 4,113,744

[45] Sep. 12, 1978

[54] MICROCRYSTALLINE 3-(ALPHA-ACETONYLBENZYL)-4-HYDROXYCOUMARIN (WARFARIN) AND METHODS OF MAKING

[75] Inventor: Nasri W. Badran, 428 Oxford Rd., New Rochelle, N.Y. 10804

[73] Assignee: Nasri W. Badran, New Rochelle, N.Y.

[21] Appl. No.: 496,932

[22] Filed: Aug. 13, 1974

[51] Int. Cl.$^2$ ............................................. C07D 311/20
[52] U.S. Cl. .................................. 260/343.44; 424/281
[58] Field of Search .................... 260/343.44, 343.2 R

[56] References Cited

U.S. PATENT DOCUMENTS

| | | | |
|---|---|---|---|
| 2,666,064 | 1/1954 | Starr et al. | 260/343.2 |
| 2,752,360 | 6/1956 | Starr et al. | 260/343.2 |
| 2,777,859 | 1/1957 | Link | 260/343.2 R |
| 2,932,652 | 4/1960 | Molnar | 260/343.2 |

OTHER PUBLICATIONS

United States Pharmacopeia, XVIII, p. 675–676, (1970).
The Van Nostrand Chemist's Dictionary, (1953), p. 105.
Pauling, College Chemistry, 3rd Ed., (1964), pp. 537–539.

Primary Examiner—Jane S. Myers
Attorney, Agent, or Firm—LeBlanc & Shur

[57] ABSTRACT

Microcrystalline 3-(alpha-acetonylbenzyl)-4-hydroxy coumarin (warfarin), having a crystal size not greater than 4.0 microns, is stable for long periods of time, is advantageous in that it is rapidly absorbed from the gastrointestinal tract and thus provides a highly desirable level of bioavailability not previously possible. It is crystallized from a buffered alkaline solution of warfarin by acidification thereof. Compositions thereof are useful for anticoagulant and rodenticide purposes, and methods of making such compositions and of using the new microcrystalline form of warfarin for such purposes are disclosed.

12 Claims, No Drawings

MICROCRYSTALLINE 3-(ALPHA-ACETONYLBENZYL)-4-HYDROXYCOUMARIN (WARFARIN) AND METHODS OF MAKING

BACKGROUND OF THE INVENTION

1. Field of the Invention

Warfarin; microcrystalline warfarin; anticoagulants; rodenticides.

2. Prior Art

The compound 3-(alpha-acetonylbenzyl)-4-hydroxycoumarin (warfarin) is well-established and widely-employed as an oral anticoagulant and rodenticide. The rodenticide effect of the compound is due to the anticoagulant and blood thinning effect of the compound acting as an anticoagulant.

The compound 3-(alpha-acetonylbenzyl)-4-hydroxycoumarin exists in both enol (acid) and keto configurations. The enol form is generically known as warfarin acid and is adopted by the U.S.P. XVIII as the reference standard for purity, being considered the active compound, despite its normal use in the form of its sodium salt. This form will hereinafter be referred to as warfarin acid, enol warfarin, or simply warfarin.

The sodium salt of 3-(alpha-acetonylbenzyl)-4-hydroxycoumarin, as described in the U.S. Pharmacopeia in its most recent revision (XVIII), under the generic name of Sodium Warfarin, page 674, shows inconsistency in its chemical composition due to its recrystalization from isopropyl alcohol in the form of a clathrate containing varying amounts of warfarin, sodium, water, and isopropyl alcohol, despite the great effort which has been exerted to obtain a pure cyrstalline compound of a definite chemical structure (see U.S. Pat. Nos. 3,077,481 and 3,246,013). These efforts were exerted because of the belief that solubility in water of the sodium salt of 3-(alpha-acetonylbenzyl)-4-hydroxycoumarin was a requirement for absorption from the gastrointestinal tract (see U.S. Pat. No. 2,777,859). It was later shown that solubility of the sodium salt in water is not the important factor in absorption of 3-(alpha-acetonyl-benzyl)-4-hydroxycoumarin from the alimentary canal, but that the sodium salt is only a convenient chemical means of providing the enol or acid form of the anticoagulant 3-(alphaacetonylbenzyl)-4-hydroxycoumarin, which is the active anticoagulant and the compound actually absorbed from the gastrointestinal tract (Robert A. O'Reilly, *Annals of the New York Academy of Sciences,* Vol. 226, pp. 293–308 [Nov. 26, 1973]). This fact has justified the elaborate work which has been undertaken to obtain sodium warfarin in a pure crystalline form. In other words, it was confirmed that the hydrophobic enol or acid form is more readily and rapidly absorbed than the hydrophilic sodium salt. What really happens, then, in the alimentary canal, is that the sodium salt is converted to the enol or acid form, which is the form actually absorbed and responsible for the anticoagulant action. Confirming this finding, the dissolution rate test for sodium warfarin tablets as published by O'Reilly, R. A. in *Bioavailability of Drugs* (1972), requires that the pharmaceutical form be exposed for thirty (30) minutes to 0.1 N hydrochloric acid, which is intended to precipitate the warfarin acid, prior to conducting the dissolution rate test at a physiological pH of 7.4. However, the warfarin acid of commerce is amorphous or large crystals and even the U.S.P. Reference Standard crystals, recrystallized from ethanol, are more than 2,000 microns in length and average 100 microns in diameter, being in the form of large needles. [This is in direct contrast to the warfarin acid crystals of the present invention which are microcrystalline in nature, not greater than 4 microns in length, ordinarily 0.1 to 4 microns in length, having an average length of 0.62 micron (average size of 20 crystals), are translucent, have sharp edges and are also needle shaped. The term "microcrystalline", by definition, is applied to crystals which in length and diameter do not exceed 10 microns. Alfonso, A. S. et. al., *Journal of Pharmaceutical Sciences* 60, No. 10, pp. 1572–1574 (Oct. 1971).]

It has also been confirmed that drugs which are insoluble in water, when administered orally in a microcrystalline form in crystal sizes below 10 microns, attain higher serum levels more rapidly than the same drugs administered in larger crystal or particle size. (Alfonso, A. S. and Nailz, V. R., *Journal of Pharmaceutical Sciences* 60, No. 10, pp. 1572–1574 [Oct. 1971]).

The warfarin acid of commerce is amorphous and is obtained chemically pure only by crystallization from ethyl alcohol. Its method of manufacture is disclosed in U.S. Pat. No. 2,752,360, which describes its purification by crystallization from hot ethyl alcohol. This warfarin acid of commerce can be used as a rodenticide, but it is not 100% pure and is known chemically to be a mixture having unknown proportions of the keto and enol warfarin. It cannot be used clinically, because only the pure enol form is desirable and acceptable by the medical profession for its anticoagulant action. The impurities inherent in the commercially available warfarin acid of commerce, moreover, cannot be removed by recrystalization from alcohol or other organic solvents. Pure warfarin from pharmaceutical and clinical use can be obtained from the commercially available product only if it is converted completely to its enol or acid form through a process which would also remove all phenolic impurities. Up to the present time, only by use and employment of the sodium salt form thereof, i.e., "Crystalline Sodium Warfarin, USP", has this been possible. For example, in the manufacture of the warfarin sodium salt (see U.S. Pat. Nos. 2,777,859, 2,765,321, and 3,077,481), the initial step calls for the use of sodium hydroxide and an excess of warfarin which acts as a buffer to avoid degradation of the warfarin molecule by the strongly alkaline sodium hydroxide. The excess of warfarin is then recovered and reused in a relatively uneconomic but continuous process of converting the warfarin to its sodium enolic salt. It would be highly desirable to have available pure warfarin acid in a different and definite crystalline form and by a process which obviated the previously unavoidable disadvantages already mentioned.

It is accordingly one object of this invention to provide directly for oral use the enol or acid form of warfarin in a pure pharmaceutical grade and of a microcrystalline structure which has hitherto not been available, and by a novel process which has likewise been hitherto unavailable.

SUMMARY OF THE INVENTION

New microcrystalline warfarin, which is stable for long periods in contrast to presently widely-used sodium warfarin USP, is much faster-absorbed from the gastrointestinal tract and thus is capable of providing a level of bioavailability which was not previously attainable. The new microcrystalline form may be obtained by crystallization from a buffered aqueous alkaline form of warfarin by acidification thereof. The microcrystalline warfarin may also be converted into suitable compositions thereof which are useful for anticoagulant and rodenticide purposes. The methods of making such compositions and the methods of using the new microcrystalline form of warfarin for such purposes also constitute a part of the present invention.

OBJECTS OF THE INVENTION

To provide new microcrystalline warfarin. To provide such product, which is stable for long periods and rapidly absorbed from the gastrointestinal tract, thereby producing a highly desirable level of bioavailability not previously possible. To provide a novel method of preparing the said microcrystalline warfarin. To provide compositions thereof which are useful for anticoagulant and rodenticide purposes. To provide a method of making such compositions. To provide a method of using the new microcrystalline form of warfarin for such purposes.

GENERAL DESCRIPTION OF THE INVENTION

According to my novel process, my objectives are accomplished in an aqueous medium in the following manner:

1. Transforming the warfarin acid of commerce (or other suitable starting material) into the warfarin enol form, through formation of a soluble salt, by employment of a buffer system. This soluble salt goes into solution, leaving the contaminents, e.g., the phenolic and other impurities present, in the insoluble state, so that they can be readily eliminated.

2. Converting the soluble salt in situ to the warfarin acid. Using my reaction conditions and sequence, the pure microcrystalline warfarin acid precipitates and may be readily recovered.

In its broadest aspects, the method of the invention comprises the steps of buffering warfarin in aqueous solution at an alkaline pH which is not destructive of the warfarin molecule, removing impurities to obtain a clear aqueous solution of the buffered warfarin, and neutralizing the buffer system to bring the solution to a lower pH at which microcrystalline warfarin acid precipitates. When the pH exceeds the range of 8-9 substantial margins before neutralization, or is substantially in excess of 7 after neutralization, loss in yield is experienced with attendant economic disadvantage. Therefore, the procedure generally includes the steps of buffering warfarin in an aqueous alkaline solution at a pH in the range of about 8-9, preferably about 8.5, removing impurities as by filtration or centrifugation to obtain a clear aqueous solution of buffered warfarin, neutralizing the buffer system to bring the solution to a pH range of 5-7, preferably about 6.5, to precipitate microcrystalline warfarin acid, and conventionally recovering the precipitate. The selected starting material may illustratively be impure warfarin acid, which may be the warfarin acid of commerce, or crystalline sodium warfarin, either impure or pure, or another water-soluble warfarin salt. An amine buffer system is preferably employed, an organic acid such as citric acid is preferably employed for the acidification, and the acid is preferably added to the buffered solution with vigorous stirring and at or about room temperature, although other reagents and conditions may also be employed. The microcrystalline warfarin product may then be used to increase the clotting time of blood in vivo, preferably in the usual manner by oral administration to mammals, including humans; in the preparation of pharmaceutical compositions including a pharmaceutically acceptable carrier for such purpose; in the killing of rodents by the oral administration thereto; and in the preparation of rodenticide compositions including a rodenticidally-acceptable carrier therefor. Preparation of the pharmaceutical compositions is by admixture with the usual pharmaceutically acceptable carriers. Preparation of the rodenticide compositions is by admixture with the usual rodenticidally acceptable carriers. In use or application, the effect of the compositions embodying the microcrystalline warfarin is relatively greater stability and more rapid and greater effectiveness at equal dosages or amounts due to the greater and more rapid bioavailability of the warfarin in microcrystalline form from the gastrointestinal tract.

STARTING MATERIAL

Starting material for the method of the invention is most advantageously the warfarin acid of commerce which is the rodenticide grade and not more than about 98% pure. Other impure warfarin may be employed as starting material, as may also be "Crystalline Sodium Warfarin U.S.P." or grades of lesser purity of this or other warfarin salts. The choice of warfarin or warfarin salt starting material is dictated mainly by economy, for which reason the warfarin of commerce is presently preferred.

SOLVENT

The solvent for the method of the present invention can be exclusively water, preferably purified or distilled water, and no organic solvents such as the conventional alcohol or ketones, particularly ethyl alcohol or isopropyl alcohol, are required. The ability to employ water and conduct the entire process for the preparation of microcrystalline warfarin in such exclusively aqueous medium is one of the salient advantages of the invention, especially from the standpoint of economy and convenience and elimination of unnecessary steps. It will, of course, be understood that should one wish to carry out the process of the invention in a less than optimum fashion, various amounts and types of solvents may be employed, so long as the medium still remains aqueous and the product still remains microcrystalline, although obviously greatest advantage will accrue to the employment of an exclusively aqueous system, as will be apparent to one skilled in the art.

BUFFER SYSTEM

Any suitable buffer system which will act to buffer, that is, permit small variations of pH within, the aqueous warfarin enol-acid salt solution in the pH range between 6 and 10, may be employed. Among such buffer systems may be mentioned sodium and ammonium acetate, sodium citrate, phosphate buffers such as sodium or potassium monobasic phosphates (See U.S.P. XVIII, Page 939). Mixtures of buffering agents may also be employed. Numerous amine buffers have the required capacity, and are accordingly preferred. Amino acid buffers (having an amine group) are included within the generic term "amine buffers." The buffer employed should not itself provide elements or groups which will precipitate upon lowering the pH to about 6-7.

AMINE BUFFERS

Numerous amine buffers are commercially available and may be employed alone or as mixtures. The preferred amine buffers are set forth in Table I, additional amine buffers being set forth in Table II, and amino acid buffers being set forth in Table III.

Amine buffered solutions have the unique characteristics of allowing ready accomplishment of the two objectives set forth in the foregoing, viz., transformation of the warfarin acid to its enol form through formation of a soluble salt, and conversion of the soluble salt in situ to the warfarin acid upon acidification, and moreover may be filtered clear. Amine buffers are particularly useful because they offer a wide variety of stable buffer systems within the pH range of 6–10 in the presence of the acidic warfarin molecule. Of course, any amine or other buffer which would not provide such a stable buffer system with the water-soluble acidic warfarin molecule within this pH range would not be useful, as will be apparent to one skilled in the art. However, the examples of the amine buffers set forth in the following Tables are not to be construed as limiting, since additional amines which act similarly may also be employed by one skilled in the art for the establishment of stable buffered system including a warfarin enol-acid salt within the pH range of, e.g., 7–10 or about 8–9, and then lower at a pH of about 5–7, in accord with the teaching of the present invention.

TABLE I

| Amine buffer | pH range |
|---|---|
| Ethylenediamine | 6.0 – 8.0 |
| Triethanolamine | 6.8 – 8.8 |
| Tris-(hydroxymethyl)-aminomethane | 7.0 – 9.0 |
| 2-Amino-2-methyl-1,3-propanediol | 7.8 – 9.8 |
| Diethanolamine | 7.9 – 9.9 |

TABLE II

| Amine buffer | pH range |
|---|---|
| 4-Aminopyridine | 8.1 to 10.1 |
| Ammonia | 8.2 to 10.2 |
| Ethanolamine | 8.5 to 10.5 |
| 2-Amino-2-methyl-1-propanol | 8.7 to 10.7 |
| Hexamethylenediamine | 9 to 12 |
| Piperidine | 10.1 to 12.1 |

TABLE III

| Aminoacid buffer | pH range |
|---|---|
| Glycylglycine | 7.2 to 9.2 |
| Serine | 8.2 to 10.2 |
| Glycine | 8.8 to 10.8 |
| alpha-Alanine | 8.8 to 10.8 |
| beta-Alanine | 9.2 to 11.2 |
| gamma-Aminobutyric acid | 9.5 to 11.5 |

REMOVAL OF IMPURITIES

Any convenient procedure for the removal of non-dissolved impurities may be employed, such as filtration or centrifugation. Filtration is preferred, as it is most convenient. Usual techniques may be employed, including the use of activated charcoal, diatomaceous earth, or like conventional filter acids for purposes of effecting maximum purification, if desired. The filtrate is the clear buffered solution of warfarin acid, having a pH within the range of about 8–9, and especially about 8.5.

NEUTRALIZATION OF BUFFER

After removal of impurities, the warfarin acid solution at the pH of about 8 to 9, preferably about 8.5, is treated to neutralize the buffer and cause precipitation of the micro-crystalline warfarin acid. The degree of neutralization required for this precipitation is that sufficient to bring the pH of the solution to between about 5 and 7, preferably about 6.5. Addition of the neutralizing agent, which may be of any suitable type which does not interfere with precipitation of the warfarin microcrystals, is preferably slow and with stirring or other agitation, preferably vigorous stirring, and at room temperature. Addition of the neutralizing agent at too rapid a rate or using excess acid which shifts the pH to less than about 5 generally defeats the objects of the present invention, since at pH, even a local pH, of less than 5, the warfarin acid precipitates as macrocrystals or amorphous particles which do not possess the desirable properties of rapid absorbability and bioavailability, or the chemical, physical, pharmaceutical, and pharmacological stability of the microcrystalline warfarin acid.

ACIDS AND ACID ADDITION

Any suitable organic or mineral acid which does not interfere with the desired precipitation of microcrystalline warfarin acid may be employed for the neutralization step. As already stated, the acid is preferably added slowly, sometimes even by dropwise addition, with vigorous stirring or other agitation. This step may be conveniently conducted at room temperature. The acid must be capable of neutralizing the buffer to a stabilized pH range of about 5 to 7 and preferably about 6.5. Examples of acids which may be employed are the mineral acids, e.g., hydrochloric or phosphoric, the organic acids, e.g., formic, acetic, propionic, soluble dibasic acids, citric, tartaric, sodium or other alkali metal acid citrate, as well as sodium or potassium or other alkali metal dihydrogen phosphate. For purposes of the neutralization, any acid supplying hydrogen ions or protons in sufficient amount for reduction of the pH to the desired level may be employed, and addition of the acidic material should be at a rate sufficiently slow so that the pH of the solution shifts slowly downwardly in the presence of the buffer to the pH required for microcrystallization to occur.

DOUBLE ADJUSTMENT

It is frequently convenient or desirable, whether using an amine buffer or other buffer means for buffering the warfarin within the range of about 8–9, preferably about pH 8.5, to first employ buffer sufficient to buffer the solution within the upper portions of the range 6–10 and then to effect a downward adjustment into the pH range of 8–9 and preferably to about 8.5. This downward adjustment can be conveniently effected using an acid or an alkali metal or ammonium salt, illustratively sodium, potassium, or ammonium bisulfite or metabisulfite, preferably sodium bisulfite or metabisulfite. Adding an excess of amine solution, for example, to reach a pH of 10, is not harmful to the warfarin molecule as would be the case if sodium hydroxide were used, but in such case the pH of the solution shoud be readjusted before filtration to the preferred range of about 8–9, with a suitable acid or soluble alkali metal or ammonium salt of an acid, which acid may be either inorganic or organic, in order to obtain a solution of pure warfarin acid devoid of impurities.

When the buffer system is itself insufficiently alkaline to effect total dissolution of the warfarin in the form of its enol acid salt, the dissolution may be effected by the employment of minor amounts of stronger alkali, even sodium or potassium hydroxide, ammonium hydroxide, or the like, provided only that the stronger alkali is employed cautiously and in minimal amounts as may be required to effect the dissolution but yet not destroy the warfarin molecule or upset the effectiveness of the buffer system employed and its ability to effectively buffer the solution in the pH range of 6-10. In case such stronger alkali is employed for dissolution, however, the maximum pH of the solution should be maintained at no greater than about 8.5-9.0.

GENERAL EXAMPLE

The following general example serves to illustrate a suitable and preferred manufacturing procedure for microcrystalline 3-(alpha-acetonylbenzyl)-4-hydroxycoumarin.

Warfarin acid commercial grade 98% is mixed with approximately 10 times its weight of purified water with stirring. The slurry may be treated at any convenient temperature of 0° to 90° C. with a solution containing approximately 10% w/v of one of the amine buffer compounds mentioned above. The amine solution is added slowly with adequate stirring until the pH of the mixture is found to be stable, preferably for not less than 15 minutes, within the pH range of 8.0 to 9.0 and preferably 8.5. The solution is conventionally filtered. The clear filtrate, at room temperature, is adequately stirred during the slow addition of a 10 percent solution of citric acid, U.S.P. until the pH of the mixture is within the range of 5.0 to 7.0, and preferably within a pH range of 5.5 to 6.5, and remains stable, preferably for not less than 15 minutes, within this range. Adequate stirring is continued for 2 to 3 additional hours. Then the precipitated microcrystalline product is conventionally filtered and washed with purified water until the filtrate is virtually neutral. It is dried in a vacuum or regular dryer at a temperature not exceeding 105° C to a moisture content of not more than 1.0%.

DETAILED DESCRIPTION OF THE INVENTION

The following Examples are given by way of illustration only.

EXAMPLE 1

10 Grams of warfarin acid commercial grade (98% purity) are mixed with 100 ml. of purified water with stirring until a uniform slurry is obtained. 20 grams of triethanolamine U.S.P. are dissolved at room temperature in 200 ml. of purified water U.S.P. Add the required amount of this solution slowly to the slurry of warfarin, at a temperature of 40° C while stirring, until the pH of the solution is approximately 9.0 and remans so for 15 minutes. A 10% solution of sodium metabisulfite is added, dropwise, until the pH of the solution shifts back to approximately 8.5 and remans stable for 15 minutes. Filter immediately. Wash filter with purified water. Combine filtrate and washings. Solution is crystal clear, pH of filtrate 8.5. Dissolve 25 g. citric acid U.S.P. in 500 ml. of purified water at room temperature. Add this solution gradually to the clear filtrate with adequate stirring, preferably vigorous, until pH of mixture is approximately 6.0 (5.5 to 6.5). Continue stirring for 2 additional hours. Leave to stand for 5 to 10 hours to complete crystallization. Filter and wash the precipitated microcrystals with purified water U.S.P. until pH of filtrate is same as pH of the purified water used for washing. Transfer the white microcrystals to a stainless steel or Pyrex tray and dry at a temperature not exceeding 105° C until moisture content is not more than 1.0% by weight.

EXAMPLE 2.

Same as Example 1 except that the amine buffer solution used is 20 grams of Tris (hydroxy methyl) amino methane, pure chemmical grade 99% m.p. 168°-170° C, in 200 ml. of purified water U.S.P.

EXAMPLE 3

Same as Example 2 except that the amine buffer solution is added to the warfarin slurry at a temperature of 70° to 80° C, adjusted to pH 8.5 with sodium metabisulfite, and filtered hot after addition of 0.5 grams of activated charcoal Darco-G60 (TM-Atlas). The filtrate and washings are combined, left to cool to room temperature overnight, and treated the next day with the citric acid solution to a pH of 6.0.

EXAMPLE 4

Same as Example 3 except that the amine buffer solution is the same as in Example 1.

EXAMPLE 5

The procedure is that of Example 3, but the batch size is scaled up to employ 100 grams warfarin commercial grade 98%. The yield of microcrystalline 3-(alpha-acetonylbenzyl)-4-hydroxycoumarin obtained is 83.5 grams. Results of analysis of the product from this Example (referred to as the "sample") are as follows:

| Elemental Analysis: | | | |
|---|---|---|---|
| Found: | % Carbon: 73.87 | Theor: | 74.0128% C. |
| | % Hydrogen: 5.24 | | 5.2305% H. |

Description:
White crystalline powder insoluble in water, moderately soluble in methanol, ethanol, isopropanol. Soluble in acetone, dioxane, chloroform. Freely soluble in alkaline aqueous solutions.

Microscopic examination:
The sample is examined using an Olympus (TM) binocular microscope at 400X, 600X, 1000X, 1500X. The average size of 20 crystals is 0.62 microns in length. The crystals are translucent, have sharp edges, and are needle shaped. Substantially no crystals are greater than 4 microns in length, and the crystals range from 0.1 to 4 microns in length. They are accordingly "microcrystalline". [The term "microcrystalline", by definition, is applied to crystals which in length and diameter do not exceed 10 microns. Alfonso, A. S. et al., *Journal of Pharmaceutical Sciences* 60, No. 10, pp. 1572-1574 (Oct. 1971).]

Infrared absorption spectrum:
The infrared curves, 2.5 to 15 microns, of the sample, U.S.P. Reference Standard, and a Polystyrene Test Film are compared. The test film is used as a calibration check for the spectrophotometer and is made just prior to running the standard and sample curves.

Both standard and sample are treated as follows: A sample of 0.4 mg. is weighed out on a Roller-Smith Microbalance and transferred to an agate mortar. 40 mg. of I.R. Grade Potassium Bromide, previously dried, is weighed out and transferred to the agate mortar. The substances are finely ground and mixed using an agate pestle. The mixture is then transferred to a Beckman Minidie (TM). The minidie was then closed and a vacuum applied for 2 minutes. The minidie bolts were then tightened by hand wrenches and the vacuum continued another 3 minutes. The curve was then run on a Perkin-Elmer (TM) Model 700 Infared Spectrophotometer.

The sample and standard curves obtained have maxima only at the same wavelengths. The materials tested are identical.

Moisture content by drying to constant weight at 105° C.

The U.S.P. XVIII method for loss on drying is used to obtain the moisture content of the sample. The moisture content was found to be 0.72%.

Melting Range:

The U.S.P. XVIII method class 1a is used to obtain the M.R. of both the U.S.P. standard and the sample of microcrystalline 3-(alpha-acetonylbenzyl)-4-hydroxycoumarin. In addition, the mixed melting point determination is used as confirmatory evidence of chemical identity.

The results are tabulated below:
Sample: = 161.0°-161.5° C.
U.S.P. standard = 161.0°-161.5° C.
Mixed = 161.0°-161.5° C.

Assay on the anhydrous basis:

The procedure in U.S.P. XVIII under Sodium Warfarin "Assay" is used with the following modifications:

The sample solution is prepared exactly the same as the standard solution since the sample is warfarin acid and not the sodium salt. The factor (1.071) is omitted from the calculation for the same reason.

The U.S.P. standard is dried to constant weight by the same method as employed in "Moisture Content by Drying". The sample was used "as is" and the moisture content determined under "Moisture Content by Drying" was used to correct for the moisture content of the sample. The sample is found to be 99.4% warfarin calculated on an anhydrous basis. Copies of the standard and sample solution scans were made on a Beckman DB ultraviolet recording spectrophotometer from 320 to 240 nm and showed the materials to be identical.

Analytical conclusions:

Microcrystalline 3-(alpha-acetonylbenzyl)-4-hydroxycoumarin is a microcrystalline form of warfarin, is chemically identical to the U.S.P. XVIII Warfarin Reference Standard as evidenced by examination of its melting range tets, mixed melting point tests, infrared potassium bromide pellet curves 2.5 to 15 microns, ultraviolet curves from 320 to 240 nm, and its quantitative analysis by the U.S.P. XVIII method.

Biological:

Upon oral administration, sodium warfarin precipitates in the acid medium of the stomach to form crystals which are variable in size. The microcrystalline warfarin, on the other hand, is not affected by the stomach acid, and is more evenly and rapidly absorbed in accord with the microcrystalline hydrophobic (acidic) phenomenon hypotheses of O'Reilly, et al. and Alfonso, et al., supra. Upon oral administration to mammals, therefore, the microcrystalline warfarin acid exhibits more rapid anticoagulant effect, as well as an increased dissolution rate when compared with sodium warfarin under similar conditions as shown by *in vitro* tests.

6. OTHER EXAMPLES

Additional examples according to the procedure of Examples 1-5 but employing the different buffer systems and acids set forth hereinbefore under "Buffer Systems" and "Acids and Acid Addition" are also effective in producing the desired microcrystalline warfarin acid.

Pharmaceutical Compositions and Their Method of Preparation and Use

The microcrystalline warfarin acid of the present invention may be employed in the usual manner and in usual pharmaceutical forms for the control of the clotting time of blood by the oral administration to mammals, including humans. Since the microcrystalline warfarin is a highly active anticoagulant, its effect is to increase the clotting time of blood and, in this capacity, the microcrystalline warfarin appears, like other 4-hydroxycoumarin anticoagulants, to act by preventing the formation and retraction of thrombi. It is administered in the same manner as conventional 4-hydroxycoumarin anticoagulants and in the same pharmaceutical forms, preferably with a pharmaceutically-acceptable carrier or excipient, at or about the same dosage levels as previously employed for Sodium Warfarin U.S.P., although somewhat lower dosages may be employed due to the rapid absorption and high degree of bioavailability of the active anticoagulant warfarin acid in its microcrystalline form. The literature is replete with references to the various pharmaceutical forms and carriers, excipients and binders which may be employed, and reference is made to tablets, capsules, granules, lozenges, solutions, suspensions, and elixirs, and to lactose, starch, talc, and magnesium stearate, to name only a few.

Further reference may be made to Remington on Pharmacy, to the Physician's Desk Reference, 28th Ed., 1974, and to U.S. Pat. Nos. 3,007,481 and 3,246,013 and especially to the publications cited therein, as to the use of warfarin sodium as an anticoagulant and to dry, stable compositions suitable for oral administration, in which the microcrystalline warfarin acid of the present invention may be embodied or substituted directly for warfarin sodium with the same or superior results.

Representative Pharmaceutical Dosage Forms

A. Example of a Tablet Formula containing 10 mg. of microcrystalline 3-(alpha-acetonylbenzyl)-4-hydroxycoumarin (warfarin)

| | |
|---|---|
| Microcrystalline warfarin, fine powder | 10.mg. |
| Lactose U.S.P. powder | 190.mg. |
| corn Starch 1551 food grade | 5.mg. |
| Water (Sufficient quantity to granulate) The granulation is dried at 40° C in a pharmaceutical dryer on trays in a conventional way to a moisture content of 0.1 to 0.2%. The dried granulate is screened using conventional equipment. The screened dry granulate is blended with the following lubricants: | |
| Starch U.S.P. | 18.mg. |
| Magnesium Stearate U.S.P. | 2.mg. |
| Then compressed into tablets 250 mg. each using suitable punch and compressing machine. | |

B. Example of a Capsule Formula containing 10 mg. of Same Compound

| | |
|---|---|
| Microcrystalline warfarin, fine powder | 10.mg. |
| Lactose U.S.P. powder | 190.mg. |
| Magnesium Stearate U.S.P. | 5.mg. |
| Blend and encapsulate using a suitable capsule size and conventional equipment. | |

Other aspects of my invention, accordingly, include the following: in a method of increasing the clotting time of blood in a mammal using an orally-effective anticoagulant, the improvement which comprises employing microcrystalline warfarin as the anticoagulant; such method wherein the microcrystalline warfarin is administered in combination with a pharmaceutically-acceptable carrier; and such method wherein the mammal is a human. Also, pharmaceutical compositions comprising an effective amount of an orally-effective antiocoagulant and a pharmaceutically acceptable carrier, characterized in that the orally effective anticoagulant is microcrystalline warfarin. Moreover, in a method of making a pharmaceutical composition including an orally-effective anticoagulant and a pharmaceutically acceptable carrier, the improvement which comprises admixing an orally-effective amount of microcrystalline warfarin and a pharmaceutically acceptable carrier.

Rodenticide Composition and Their Method of Preparation and Use

The microcrystalline warfarin acid of the present invention may be employed in the usual manner and in usual rodenticide forms for the control of rodents, especially rats and mice but including other rodents, even vampire bats. Since the microcrystalline warfarin is a highly active anticoagulant, its effect is to increase the clotting time of blood and, in its capacity as a rodenticide, the microcrystalline warfarin appears, ike other 4-hydroxycoumarin anticoagulant rodenticides, to act by a blood-thinning and anemia-producing mechanism. It may be administered to rodents in the same manner as conventional 4-hydroxycoumarin anticoagulant rodenticides and in the same rodenticidal forms, preferably with a rodenticidally acceptable carrier or excipient, at or about the same dosage levels as previously employed for Sodium Warfarin or impure warfarin acid rodenticide, although somewhat lower dosages may be employed due to the rapid absorption and high degree of bioavailability of the active anticoagulant rodenticide warfarin acid in its microcrystalline form. The literature is replete with references to the various rodenticidal baits and forms and carriers and excipients and rodent attractants which may be employed, and reference is made to corn, grain, brans, mash, water, sand, diatomaceous earth, mineral oil plus corn syrup solids, and fruit flavors, to name only a few, in addition to usual capsules and tablets for water baiting, and in addition to combinations with any other food or foodstuff acceptable and advantageously attractive to the rodent. Further reference may be made to U.S. Pat. Nos. 2,687,365, 2,783,177, 3,258,396, 3,268,402, 3,816,610, and 3,818,100, and to the publications cited therein, as to the use of warfarin of commerce or warfarin sodium as an anticoagulant rodenticide and to compositions and combinations suitable for rodenticidal administration and use, in which the microcrystalline warfarin acid of the present invention may be embodied or substituted directly for warfarin sodium with the same or superior results

Representative Rodenticide Formulations and Applications

Example 1: Compositions for Rodenticide Use

A mixture of the microcrystalline warfarin is prepared by blending 0.5 parts by weight with 99.5 parts by weight of a diluent such as corn starch or sugar powder. One part of this mixture is blended with 19 parts of a food product, acceptable to mice or rats, for example corn meal, and provides a finished food bait which contains 99.975 parts of food and 0.025 part of the microcrystalline warfarin. This concentration is considered outstanding in food bait, as it allows the intake by the rodent of relatively minute amounts several times of the rodenticide microcrystalline warfarin. This multiple doses concept produces high kills in both rats and mice within a few days.

2. Other Examples

Substitution of equal or lesser quantities of microcrystalline warfarin in any rodenticide composition for the active ingredient thereof produces highly satisfactory rodent kills when employed in the usual manner. Reference is made, for example, to U.S. Pat. Nos. 2,783,177 and 2,687,365 for further rodenticide carriers and compositions.

Still additional aspects of my invention are, accordingly: in a method of killing a rodent employing an orally-effective anticoagulant rodenticide, the improvement which comprises employing microcrystalline warfarin as the orally-effective anticoagulant rodenticide. Also, a rodenticide composition comprising an effective amount of an orally-effective anticoagulant rodenticide composition in admixture with a rodenticidally acceptable carrier, characterized in that the orally-effective anticoagulant rodenticide is microcrystalline warfarin. Moreover, in a method of making a rodenticide composition including the step of admixing an orally-effective anticoagulant rodenticide with a rodenticidally acceptable carrier therefor, the improvement which comprises admixing microcrystalline warfarin with a rodenticidally acceptable carrier.

The present invention, among other advantages, permits accomplishment of the following novel objectives which have hitherto been unavailable:

1. The manufacture of a pharmaceutically and chemically pure microcrystalline grade of 3-(alpha-acetonyl-benzyl)-4-hydroxycoumarin from commercially available warfarin acid, the rodenticide grade, which is not more than 98% pure.

2. Production of pure microcrystalline warfarin in exclusively aqueous medium and not employing the common methods of recrystallization using organic solvents, particularly ethyl alcohol, presently in use as the main solvent employed for the crystallization of warfarin, or isopropyl alcohol, which is normally used for the crystallization of Sodium Warfarin.

3. A standardized product with definite description and specifications by far superior to the commonly used Sodium Warfarin U.S.P.

4. A microcrystalline form of warfarin which is most desirable for fast absorption and improved bioavailability.

5. An extremely stable material useful for the preparation of stable pharmaceutical and rodenticidal dosage forms.

It is to be understood that the invention is not to be limited to the exact details of operation or exact compounds, compositions, methods, or procedures shown and described, as obvious modifications and equivalents will be apparent to one skilled in the art.

I claim:

1. Method for the production of warfarin acid crystals having a length of from 0.1 to 4 microns comprising the steps of dissolving warfarin in aqueous solution at an alkaline pH of 7–10 with a buffer selected from the group comprising sodium acetate, ammonium acetate, sodium citrate, phosphates, amines and mixtures thereof, bringing the obtained solution to a specific pH of 8.0 to 9.0, removing impurities by filtration or centrifugation to obtain a clear aqueous solution of the buffered warfarin, and neutralizing the buffer system to bring the solution to a pH of 5.0 to 7.0 at which the microcrystalline warfarin acid precipitates and recovering the precipitated microcrystalline warfarin.

2. Method of claim 1, wherein an amine buffer is employed.

3. Method of claim 2, wherein the warfarin enol-acid is buffered in aqueous medium at a pH of about 8.5, and the buffer system is neutralized to a pH of about 6.5.

4. Method of claim 2, wherein the amine buffer is selected from the group consisting of: ethylenediamine, triethanolamine, tris-(hydroxymethyl)-aminomethane, 2-amino-2-methyl-1, 3-propanediol, and diethanolamine.

5. Method of claim 2, wherein the buffer system is neutralized with an organic acid.

6. Method of claim 5, wherein the buffer is neutralized using an acid selected from the group consisting of: formic acid, acetic acid, propionic acid, citric acid, tartaric acid, and alkali metal acid citrate, hydrochloric acid, phosphoric acid, and an alkali metal dihydrogen phosphate.

7. Method of claim 1, wherein the downward adjustment of pH to within the preferred pH range of about 8–9 is effected using an acid or an alkali metal or ammonium bisulfite or metabisulfite.

8. Method of claim 7, wherein the downward pH adjustment is effected using a compound selected from the group consisting of sodium metabisulfite and sodium bisulfite.

9. Method of claim 1, wherein the impurities are removed by filtraton and wherein a filter aid is employed to assist with filtration.

10. Method of claim 1, wherein the pH is buffered at about 8.5 using an amine buffer, impurities are removed by filtration, and the pH adjusted downwardly by slow addition of citric acid to a pH of about 6.5 and with vigorous agitation.

11. Method of claim 10, wherein the buffer is tris-(hydroxymethyl)-aminomethane.

12. Microcrystalline warfarin acid, (3-alpha-acetonyl-benzyl-4-hydroxy coumarin), having a crystal size ranging from 0.1 to 4.0 microns in length, having an average (of 20) crystal length of about 0.62 microns, being translucent, having sharp edges and being needle shaped.

UNITED STATES PATENT AND TRADEMARK OFFICE
CERTIFICATE OF CORRECTION

PATENT NO. : 4,113,744
DATED : September 12, 1978
INVENTOR(S) : NASRI W. BADRAN

It is certified that error appears in the above-identified patent and that said Letters Patent are hereby corrected as shown below:

```
Col.  6, line 62, "shoud" should read --should--.
Col.  7, line 55, "remans" should read --remains--.
Col.  7, line 58, "remans" should read --remains--.
Col.  8, line 10, "chemmical" should read --chemical--.
Col.  8, line 36, "74.0128% C." should read --74.0138% C.--.
Col. 11, line 20, "antiocoagulant" should read --anticoagulant--.
Col. 11, line 39, "ike" should read --like--.
Col. 14, line 16, "filtraton" should read --filtration--.
```

Signed and Sealed this

Fifth Day of December 1978

[SEAL]

Attest:

RUTH C. MASON
Attesting Officer

DONALD W. BANNER
Commissioner of Patents and Trademarks